United States Patent [19]

Mody et al.

[11] Patent Number: 4,640,821
[45] Date of Patent: Feb. 3, 1987

[54] ANALYSIS APPARATUS

[75] Inventors: Dinesh I. Mody, Bedford; James E. Rasmussen, Hyde Park; Mikhail Y. Ryaboy, Methuen, all of Mass.

[73] Assignee: Fisher Scientific Company, Pittsburgh, Pa.

[21] Appl. No.: 756,149

[22] Filed: Jul. 16, 1985

[51] Int. Cl.$^4$ .................. G01N 27/26; G01N 35/08
[52] U.S. Cl. ............................ 422/81; 204/409; 422/82; 436/52; 436/150
[58] Field of Search .......... 422/81, 67, 103, 86; 204/409–411, 420; 436/52, 150

[56] References Cited

U.S. PATENT DOCUMENTS

| | | | |
|---|---|---|---|
| 3,549,994 | 12/1970 | Rothermel et al. | 422/81 |
| 3,609,040 | 9/1971 | Kuzel | 356/36 |
| 3,613,729 | 10/1971 | Dora | 137/624.18 |
| 3,900,289 | 8/1975 | Liston | 23/230 |
| 3,915,829 | 10/1975 | Krebs | 204/420 |
| 3,917,523 | 11/1975 | Stein et al. | 204/409 |
| 3,934,611 | 1/1976 | Gachot et al. | 137/608 |
| 3,951,167 | 4/1976 | Howell et al. | 137/608 |
| 3,963,440 | 6/1976 | Stein et al. | 23/253 |
| 4,108,602 | 8/1978 | Hanson et al. | 23/230 |
| 4,168,294 | 9/1979 | Calzi et al. | 422/68 |
| 4,219,530 | 8/1980 | Kopp et al. | 422/69 |
| 4,283,262 | 8/1981 | Cormier et al. | 422/81 |
| 4,304,257 | 12/1981 | Webster | 137/559 |
| 4,443,407 | 4/1984 | Weinberg et al. | 422/81 |
| 4,531,088 | 7/1985 | Czaban et al. | 204/411 |

Primary Examiner—Michael S. Marcus
Attorney, Agent, or Firm—Willis M. Ertman

[57] ABSTRACT

A system for analyzing a biological fluid or the like includes a series flow loop that extends between an inlet valve array and an outlet valve array. The flow loop includes an analysis region to which a measuring system is connected in sensing relation and an accumulator chamber connected to the outlet of the analysis region. The inlet valve array is arranged to selectively and alternately connect a sample inlet port and an auxiliary fluid reservoir to the flow loop while the outlet valve array is arranged to selectively connect a controlled source of reduced pressure to the flow loop. The volume of the accumulator chamber is at least as great as the volume of the flow loop (including the analysis region) between the inlet valve array and the accumulator chamber and the system is arranged to capture reduced pressure in the flow loop, the captured reduced pressure then being used to provide the sole transfer force to gently and reliably transfer a minute quantity of fluid to be analyzed from the sample inlet port through the analysis region and at least partially fill the accumulator chamber.

11 Claims, 6 Drawing Figures

ANALYSIS APPARATUS

This invention relates to apparatus for the analysis of fluid samples and has particular application to apparatus for analysis of parameters of biological fluids such as blood.

Accurate measurement of one or more constituents of a sample of biological fluid (whole blood, plasma, urine, etc.) provides useful information for diagnosis, assistance in the control of life support devices, evaluation of the effectiveness of therapeutic measures, and the like. Often, only a limited quantity of the biological fluid is available for analysis, and a minute quantity must be located with precision and integrity (e.g., an absence of air bubbles or carryover contamination from a previous sample) relative to one or more analysis regions for exposure to constituent sensors that provide outputs related to constituents of interest in the liquid sample being analyzed.

In accordance with the invention, there is provided a system for analyzing a biological fluid or the like that comprises a series flow loop that extends between an inlet valve array and an outlet valve array and that includes an analysis region (to which a measuring system is connected in sensing relation) and an accumulator chamber connected to the outlet of the analysis region. The inlet valve array preferably is arranged to selectively and alternately connect a sample inlet port and an auxiliary fluid reservoir to the flow loop while the outlet valve array is arranged to selectively connect a controlled source of reduced pressure to the flow loop. The volume of the accumulator chamber is equal to or greater than the volume of the flow loop (including the analysis region) between the inlet valve array and the accumulator chamber and the system is arranged to capture reduced pressure in the flow loop, the captured reduced pressure then being used to provide the sole transfer force to gently and reliably transfer a minute quantity of fluid to be analyzed from the sample inlet port through the analysis region and at least partially fill the accumulator chamber.

In preferred embodiments, the accumulator chamber is of hard construction and has a volume in the range of one-five milliliters, and the reduced pressure provided by the source is in excess of ten inches of mercury relative to atmospheric pressure. The inlet valve array is arranged to selectively and alternately connect the sample inlet port and an auxiliary fluid reservoir to the flow loop.

In a particular embodiment, the system further includes a mixing chamber having a flow conduit with an inlet in the mixing chamber that is connected to the inlet valve array. Pipette means is provided for introducing a precise quantity of sample to be analyzed and diluent into the mixing chamber, and a plurality of measuring systems are connected in sensing relation to the analysis region, each measuring system including an electrochemical electrode with an ion selective membrane that is arranged for exposure to sample in the sample flow path. A common valve control arrangement for controlling the valves in the two valve arrays includes a face plate member that has a rigid surface, a flexible valve sheet that has a surface that is softer and more resilient than the face plate surface for mating engagement with the face plate surface, a network of channel portions in one of the members with a plurality of valve land portions, each valve land portion being located between two adjacent ones of the channel portions, the surfaces of the land portions being coincident with the surface of the member in which they are located, and a valve control arrangement that includes a plurality of valve actuators, each actuator being arranged to flex the sheet member between a first position in which the valve sheet surface is in mating and sealing engagement with the valve face plate surface to sealingly block flow between adjacent ones of the channel portions and a second position in which the sheet surface is spaced away from the first position to allow flow between the adjacent channel portions across the land portion corresponding to that actuator. This compact valve array controls the flow of diluted sample to and from the analysis region, as well as controlling flow of reference fluid to the analysis region and drawing excess fluid from the mixing chamber.

Other features and advantages of the invention will be seen as the following description of a particular embodiment progresses, in conjuncton with the drawings, in which.

DESCRIPTION OF PARTICULAR EMBODIMENT

Figure 1:
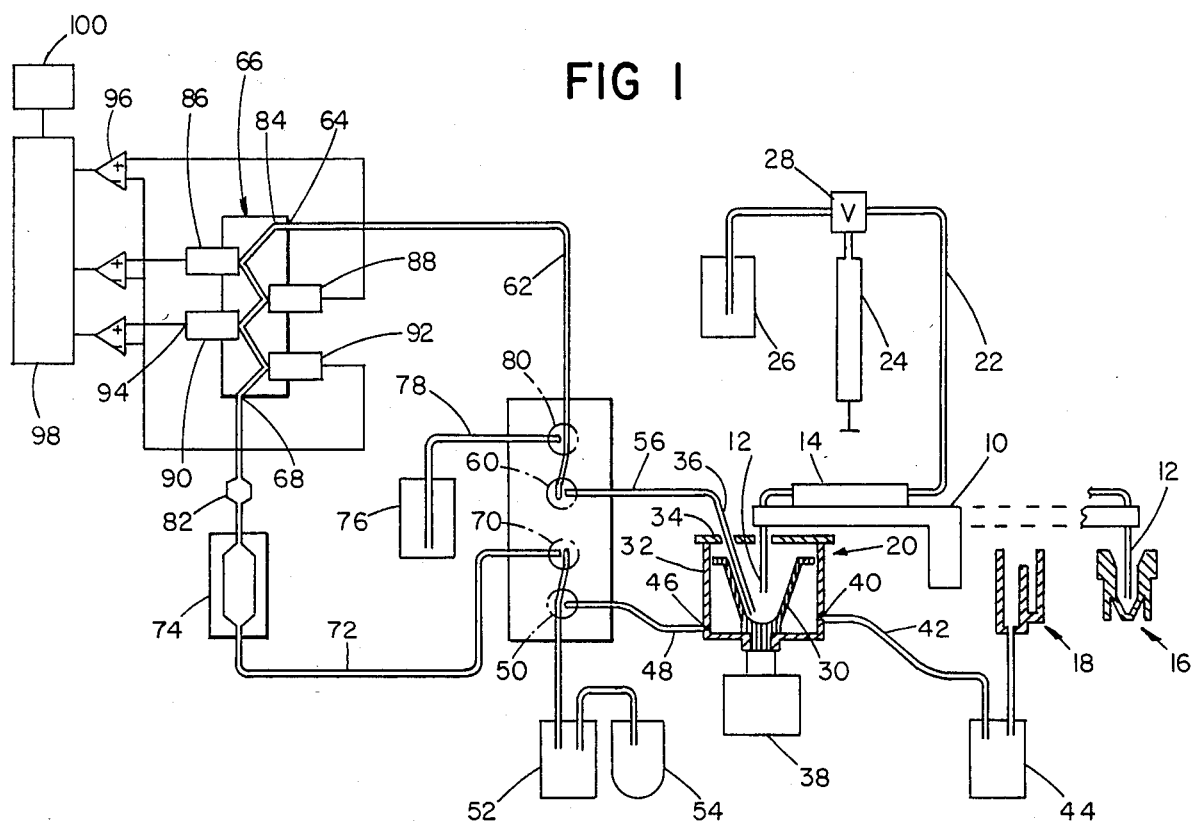
FIG. 1 is a schematic diagram of an analysis system in accordance with the invention.

Shown in FIG. 1 is a diagrammatic view of a biological fluid analysis system that includes transfer arm module 10 that carries stainless steel pipette tube 12 and liquid sensor 14 (that is utilized to detect the presence (or absence) of liquid), the transfer arm module moving the pipette tube 12 between sample station 16, washbath station 18 and mixing (spin cup) station 20. Pipette tube 12 is connected through sensor 14 and flexible tubing 22 to 500 microliter capacity positive displacement pump syringe 24 which draws buffer fluid from reservoir 26 through three-way valve 28 and delivers it to pipette tube 12.

The spin cup assembly at station 20 includes funnel-shape spin cup 30 of about six milliliter capacity and that is surrounded by plastic waste cup 32 and covered by clear plastic lid 34. A replaceable stainless steel aspirator tube 36 extends into spin cup 30, and the spin cup is driven by a reversible DC motor 38 that is located beneath the assembly. Fitting 40 on waste cup 32 is connected via overflow tube 42 to main waste bottle 44, and a second fitting 46 is connected via tube 48, control valve 50 and ISE waste bottle 52 to source 54 of precisely regulated (17±0.1 inches of mercury) reduced pressure.

Aspirator tube 36 is connected via flexible tube 56, valve 60 and tube 62 to inlet 64 of acrylic cuvette 66. Outlet 68 of cuvette 66 is connected to firm (acrylic) accumulator chamber 74 of about one milliliter capacity (the volume of the flow loop from valve 60 to chamber 74 being about one-half milliliter) and chamber 74 is connected via flexible line 72 to valve 70 which is connected to ISE waste bottle 52. Reference solution from reservoir 76 is supplied over line 78 through valve 80 and line 62 to the inlet 64 of cuvette 66.

Cuvette 66 includes a zig-zag through flow passage 84 to which sodium sensing electrode assembly 86, potassium sensing electrode assembly 88, chloride sensing electrode assembly 90, and reference electrode assembly 92 are connected. The sodium, potassium and chloride electrode assemblies each include an ion selective tip which is electrically connected to a plug in lead 94 and each of those electrode assemblies forms one half of an electrochemical cell with the nonselective reference electrode assembly 92 constituting the complimentary half of each cell. Ground coupling 82 provides the only ground potential coupling to the liquid to be analyzed and all electrolytic measurements are related to this ground. The outputs of cells 86, 88, and 90 are applied through high impedance operational amplifiers 96 to control unit 98 for analogical interpretation and calculation of the activity and concentration of sodium, potassium and chloride ions in the sample in the flow path 84 and transfer of the resulting data to output device 100.

Valves 60 and 80 form a three-way input valve to control flow through tube 62 to cuvette inlet port 64 while valves 50 and 70 form a second and similar three-way valve that applies the precisely regulated reduced pressure from source 54 either to the outlet 68 of cuvette 66 via accumulator chamber 74 or to fitting 46 of waste cup 32.

Figure 2:
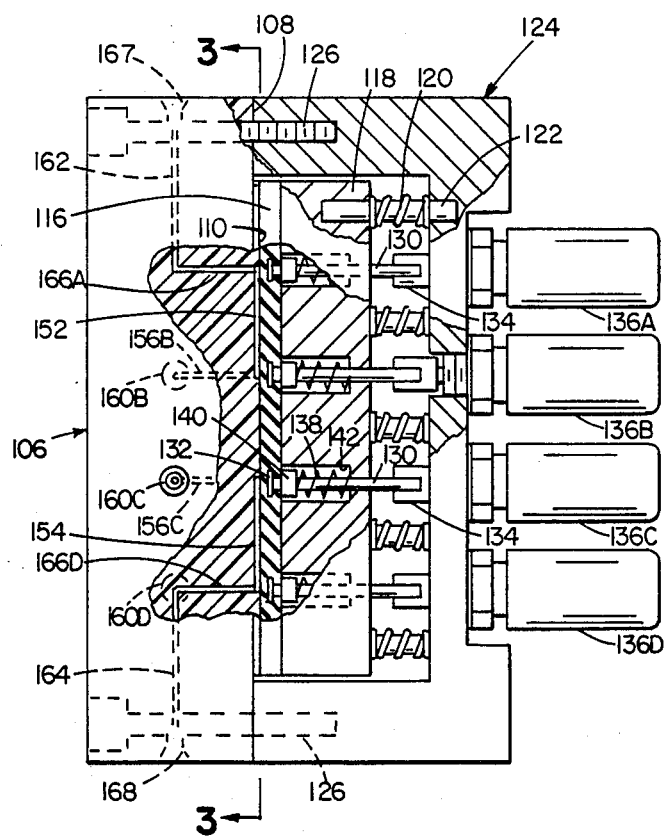
FIG. 2 is a side view (partially in section) of the valve array employed in the system shown in FIG. 1.
Figure 3:
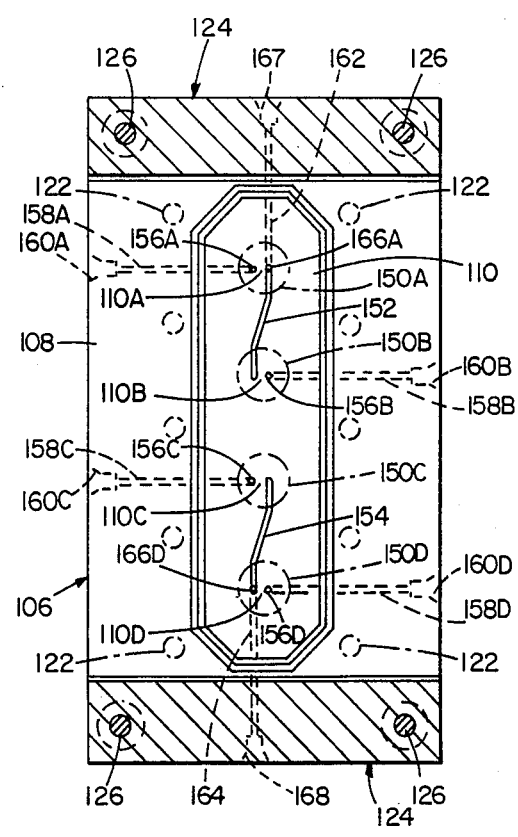
FIG. 3 is an elevational view of the valve array porting block showing details of the valves.

Further details of the valve array may be seen with reference to FIGS. 2 and 3. That valve array is of the type shown in Webster U.S. Pat. No. 4,304,257 and includes transparent porting block 106 of cast acrylic resin that has a width of about five centimeters, a length of about eight centimeters, and a thickness of about 2.5 centimeters. Formed in surface 108 of porting block 106 is a raised array of four valve lands 110 (land 110A corresponding to valve 80, land 110B corresponding to valve 60, land 110C corresponding to valve 70, and land 110D corresponding to valve 50), and clamped against surface 108 is manifold diaphragm sheet 116 that has a smooth, pit-free surface. Diaphragm sheet 116 is seated against surface 112 by backup plate 118 which is biased by springs 120 that are piloted on guide pins 122 that are received in holes in mounting block 124 and recesses in backup plate 120. Screws 126 clamp porting block 106 and mounting block 124 together.

Secured to diaphragm sheet 116 is a series of four valve actuators 130, the head 132 of each actuator being embedded in the manifold sheet 116. Each actuator 130 is connected by coupling 134 to a corresponding solenoid 136. Springs 138 that are seated between shoulders 140 of actuator rods 130 and recesses 142 of backup plate 118 bias the valve actuator rods 130 to valve closed positions.

Further details of the raised valve land array may be seen with reference to FIG. 3. That valve land array includes a set of four valve sites 150, each about one centimeter in diameter. Interconnecting valve sites 150A and 150B is a groove 152; and a similar groove 154 interconnects valve sites 150C and 150D. Each groove 152, 154 has a width of about 0.8 millimeter and a depth of about 0.8 millimeter and the bottom of each groove is a smooth radius. At each valve site, a bore 156 extends perpendicularly from its land surface 110 to a transverse passage 158 that extends to outlet port 160 which receives a tubing fitting. Similar passages 162, 164 extend from similar bores 166 at valve sites 150A and 150D to ports 167, 168 in the end walls of porting block 106. Each bore 156 is spaced from its channel 152 (154) about 0.6 millimeter with a valve land 110 therebetween. Flow through each valve is blocked by the firm seating of diaphragm 116 against land 110 in a "zero dead space" valving action. Movement of an actuator rod 130 by its solenoid 136 (an axial travel of about ¾ millimeter) moves the valve to fully open position and provides a valve chamber of frustoconical configuration. When the valve actuator 136 is released, membrane resilience supplemented by the gentle closing force of its spring 138 returns the flexed portion of diaphragm 116 to its initial seated position in a smooth, radially inward wiping action.

Figure 4:
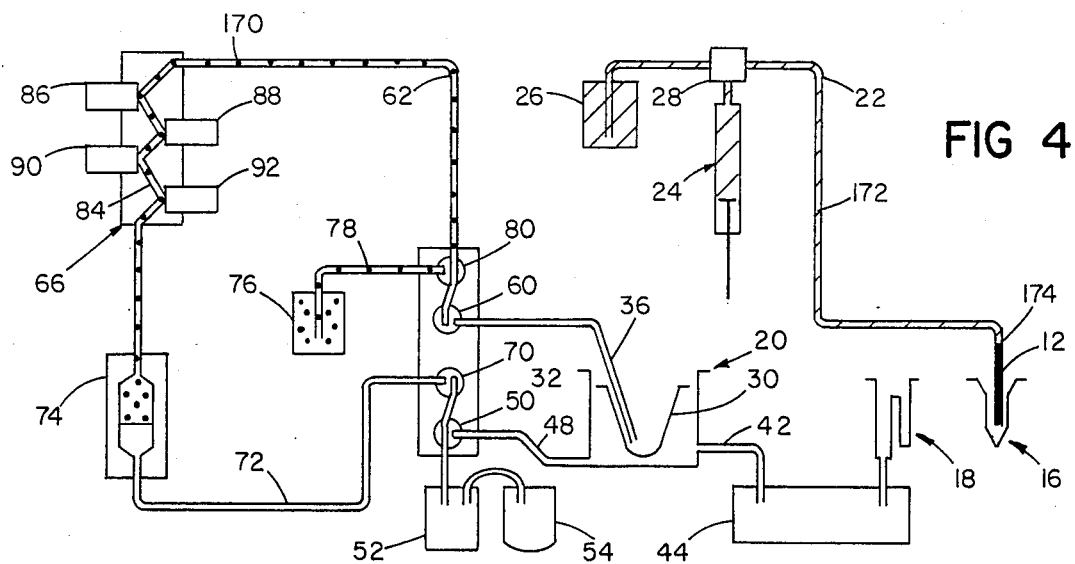
FIGS. 4–6 are diagrams showing an operational sequence of the analysis system shown in FIG. 1.
Figure 5:
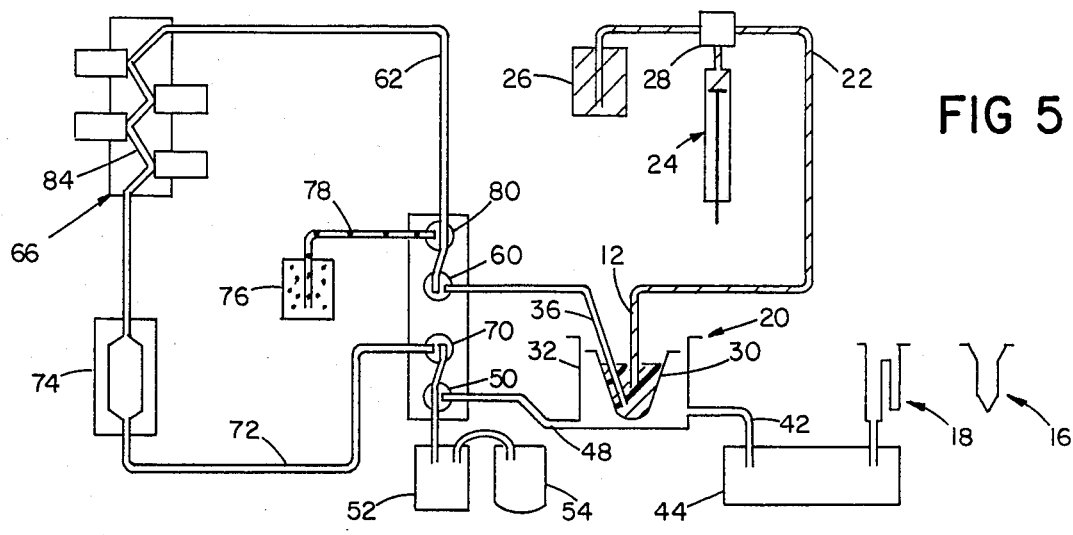
Figure 6:
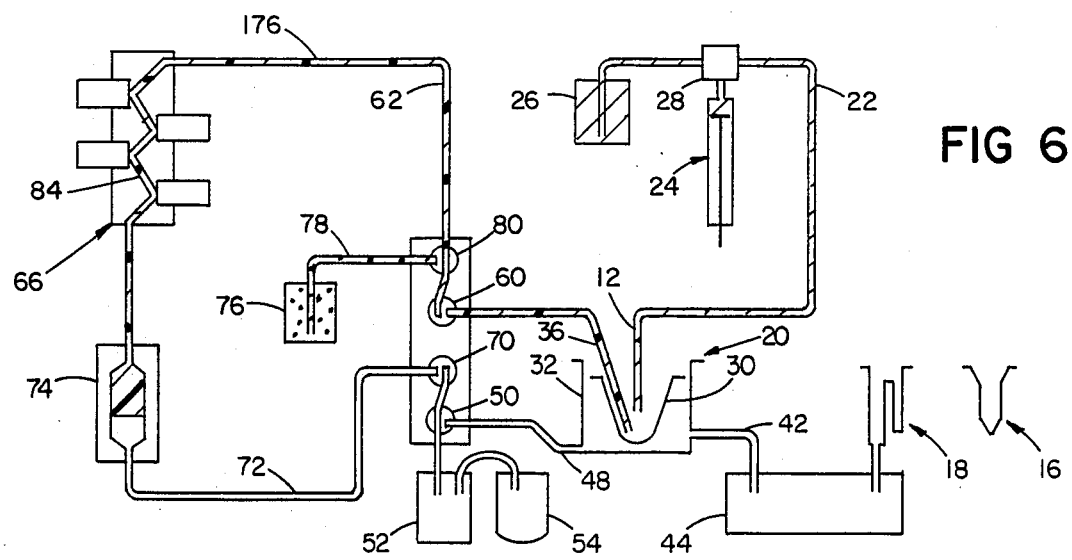

With reference to FIGS. 4–6 in system operation, with reference liquid 170 (represented by dots) in analysis passage 84 and partially filling accumulator chamber 74 and valves 50, 60, 70 and 80 closed as indicated in FIG. 4, syringe pump 24 is primed with buffer 172 (represented by light slant lines) from reservoir 26 and three-way valve 28 is then switched to pipette tube 12. With arm module 10 in the wash bath position 18, syringe 24 is operated to discharge buffer 172 into the wash bath 18. The transport arm 10 is then lifted and moved to the sample station 16, syringe 24 being partially filled with buffer 172 from reservoir 26. At sample station 16, (FIG. 4) transfer arm 10 lowers the pipette tube 12 into the sample cup and the system actuates syringe 24 to draw up a specified volume of sample 174 (or calibrator) (a typical volume of sample being thirty microliters) and then the transport arm 10 is raised and moves pipette 12 to spin cup station 20 as indicated in FIG. 5.

Before sample 174 and buffer 172 are dispensed into spin cup 30, valves 60 and 70 are opened to draw the reference solution 170 from the flow loop including analysis cuvette 66 under the influence of the reduced pressure from source 54 for discard to waste container 52; and then valves 60 and 70 are closed, as indicated in FIG. 5. Syringe pump 24 then dispenses the sample 174 along with a system specified quantity of buffer 172 (a typical volume of buffer being 1050 microliters) into cup 30. The system then operates motor 38 to drive spin cup 30 in slow speed agitation (rotating the cup 30 alternately clockwise and counterclockwise) to gently mix the sample and ISE buffer. While the sample and buffer are being mixed in the spin cup, valve 70 is opened to reduce the pressure in the flow loop including accumulator chamber 74, analysis path 84 and line 62 to the closed valve 60 to the seventeen inches of mercury reduced pressure of source 54. Valve 70 is then closed to seal the reduced pressure in chamber 74 and the flow path.

When isolation valve 60 is opened, the captured reduced pressure draws the mixed diluted sample 176 (represented by alternate heavy and light slant lines) through aspirator tube 36 and valve 60, line 62 and analysis channel 84 into accumulator chamber 74, the volume of trapped reduced pressure thus providing gentle and reliable positioning of the sample through the entire flow path 84 of cuvette 66 (FIG. 6).

Valve 60 is then closed and the spin cup 30 is driven at high speed by motor 38 to drive the excess diluted sample by centrifugal force, up and out of the spin cup into the waste cup 32. Valve 50 is then opened and the reduced pressure from source 54 is applied to line 48 and fitting 46 to drain the remaining excess sample mixture from waste cup 32.

With all valve solenoids 136 de-energized (valves closed) and the electrode cuvette flow path 84 filled with the diluted sample mixture to be analyzed, the output voltages of sensors 86, 88, 90, and 92 are monitored, and the activity and concentration of sodium, potassium and chloride ions in the sample are transmitted to the output device 100. After analysis, valves 60 and 70 are opened to flush the sample mixture from cuvette 66 and chamber 74. After the sample is flushed out with air, the valves 60 and 70 are closed, valve 60 is then opened to evacuate the chamber 74, cuvette 66 and line 62, and then closed to trap the reduced pressure in that flow loop; and then valve 80 is opened to allow the reduced pressure stored in the loop and accumulator chamber 74 to draw reference solution 170 from reservoir 76 past the electrodes 86, 88, 90 and 92, and an analysis is made of the reference solution. The reference solution remains in the cuvette 66 and accumulator chamber 74 (as shown in FIG. 4) until the next analysis sequence.

While a particular embodiment of the invention has been shown and described, various modifications will be apparent to those skilled in the art, and therefore it is not intended that the invention be limited to the disclosed embodiment or to details thereof and departures may be made therefrom within the spirit and scope of the invention.

What is claimed is:

1. A system for analyzing a biological fluid comprising:
   structure defining an analysis region having an inlet and an outlet, a measuring system connected in sensing relation to said analysis region,
   structure defining an accumulator chamber that has an inlet and an outlet, the inlet of said accumulator chamber being connected to the outlet of said analysis region,
   an inlet valve array connected to the inlet of said analysis region, an outlet valve array connected to the outlet of said accumulator chamber, structure defining a series flow path that extends between said inlet valve array and said outlet valve array and includes said analysis region and said accumulator chamber,
   said accumulator chamber having a volume at least as great as a volume defined by said series flow path, including said analysis region, between said inlet valve array and said accumulator chamber,
   structure defining a sample inlet port, means connecting said sample inlet port to said inlet valve array,
   a controlled source of reduced pressure, means connecting said controlled source of reduced pressure to said outlet valve array, said outlet valve array being arranged to selectively connect said controlled source of reduced pressure to said series flow path to apply reduced pressure to the outlet of said accumulator chamber,
   said inlet valve array being arranged to selectively connect said sample inlet port to said series flow path, and
   control means for operating said inlet valve array and said outlet valve array to initially capture reduced pressure in said series flow path, and then to open said inlet valve array so that the captured reduced pressure in said series flow path provides the sole transfer force to gently and reliably transfer a minute quantity of fluid to be analyzed from said sample inlet port through said analysis region and to at least partially fill said accumulator chamber.

2. The system of claim 1 wherein the volume of said accumulator chamber is in the range of one-five milliliters.

3. The system of claim 1 and further including an auxiliary fluid reservoir and wherein said inlet valve array is arranged to selectively and alternately connect said sample inlet port and said auxiliary fluid reservoir to said flow path.

4. The system of claim 1 and further including a mixing chamber having a flow conduit with an inlet in said mixing chamber and connected to said inlet valve array.

5. The system of claim 4 and further including pipette means for introducing a precise quantity of sample to be analyzed and diluent into said mixing chamber.

6. The system of claim 1 wherein said analysis chamber has a plurality of measuring systems connecting in sensing relation to said analysis region.

7. The system of claim 1 wherein said measuring system includes an electrochemical electrode with an ion selective membrane that is arranged for exposure to sample in the sample flow path.

8. The system of claim 1 wherein said valves are in an array that includes
   a face plate member that has a rigid surface,
   a flexible valve sheet that has a surface that is softer and more resilient than said face plate surface for mating engagement with said face plate surface,
   a network of channel portions in one of said members with a plurality of valve land portions, each said valve land portion being located between two adjacent ones of said channel portions, the surfaces of said land portions being coincident with the surface of the member in which they are located, and
   said valve control arrangement including a plurality of valve actuators, each said actuator being arranged to flex said sheet member between a first position in which said valve sheet surface is in mating and sealing engagement with said valve face plate surface to sealingly block flow between adjacent ones of said channel portions and a second position in which said sheet surface is spaced away from said first position to allow flow between said adjacent channel portions across the land portion corresponding to that actuator.

9. The system of claim 8 and further including structure defining a mixing chamber and pipette means for introducing a precise quantity of sample to be analyzed and diluent into said mixing chamber, and an auxiliary fluid reservoir, and wherein said sample inlet port is disposed in said mixing chamber and said inlet valve array is arranged to selectively and alternately connect said mixing chamber and said auxiliary fluid reservoir to said series flow path.

10. The system of claim 1 wherein said outlet valve array is arranged to selectively and alternately connect said controlled source of reduced pressure to said series flow path and said mixing chamber defining structure.

11. The system of claim 10 wherein the volume of said accumulator chamber is in the range of 1-5 milliliters.

* * * * *